(12) United States Patent
Yi et al.

(10) Patent No.: US 7,466,303 B2
(45) Date of Patent: Dec. 16, 2008

(54) DEVICE AND PROCESS FOR MANIPULATING REAL AND VIRTUAL OBJECTS IN THREE-DIMENSIONAL SPACE

(75) Inventors: Dingrong Yi, Toronto (CA); Graham Arnold Wright, Toronto (CA); Bob Sueh-Chien Hu, Palo Alto, CA (US)

(73) Assignee: Sunnybrook Health Sciences Center, Toronto, Ontario (CA)

( * ) Notice: Subject to any disclaimer, the term of this patent is extended or adjusted under 35 U.S.C. 154(b) by 1013 days.

(21) Appl. No.: 10/776,421

(22) Filed: Feb. 10, 2004

(65) Prior Publication Data

US 2005/0177054 A1    Aug. 11, 2005

(51) Int. Cl.
*G09G 5/00* (2006.01)

(52) U.S. Cl. .................... 345/156; 345/157; 345/158; 606/1

(58) Field of Classification Search ......... 345/156–158, 345/179; 606/1
See application file for complete search history.

(56) References Cited

U.S. PATENT DOCUMENTS

| | | | |
|---|---|---|---|
| 5,335,557 A | 8/1994 | Yasutake | |
| 5,576,727 A * | 11/1996 | Rosenberg et al. | 345/179 |
| 5,729,249 A | 3/1998 | Yasutake | |
| 5,792,135 A | 8/1998 | Madhani et al. | |
| 5,805,137 A | 9/1998 | Yasutake | |
| 5,923,318 A | 7/1999 | Zhai et al. | |
| 6,101,893 A | 8/2000 | Wergen | |
| 6,115,028 A | 9/2000 | Balakrishnan et al. | |
| 6,394,998 B1 | 5/2002 | Wallace et al. | |
| 6,441,577 B2 | 8/2002 | Blumenkranz et al. | |
| 6,593,907 B1 | 7/2003 | Demers et al. | |

OTHER PUBLICATIONS

Ackerman et al., SMRM Abtr. 1986, p. 1131.
Bornert et al., In-Plane Position Tracking of Medical Instruments during MRI, SMRM Abstr. 1997, p. 1925.
Cline et al., Focused US System for MR Imaging, Radiology 194: 731-737, (1995).
Coutts et al., Integrated and Interactive Position Tracking and Imaging of Interventional Tools and Internal Devices . . . , Magnetic Resonance in Medicine 198, 40:908-13.
Daniel et al., Comparison of Optical and MR-Tracking . . . , SMM Abstr. 1997, p. 1928.

(Continued)

*Primary Examiner*—Richard Hjerpe
*Assistant Examiner*—Leonid Shapiro
(74) *Attorney, Agent, or Firm*—Sharon J. Adams; Adams Law Office

(57) ABSTRACT

A device and software system with input and output capability for manipulating real and virtual objects in 3-dimensional space. The device consists of a six degree-of-freedom mechanical armature that has sensors to determine the location and orientation of a stylus and planar surface. In the input mode, manipulation of the physical armature will result in a corresponding two-dimensional, virtual image of the stylus and surface on a computer screen. The armature also has motors to automatically change the armature location and orientation in order to generate a physical representation in the real world of the location and orientation of a virtual object. The armature is built so that it maintains balance at any location and orientation to statically maintain the armature location and orientation without drifting to a null rest position.

57 Claims, 9 Drawing Sheets

OTHER PUBLICATIONS

Debbins et al., Cardiac Magnetic Resonance Fluoroscopy, Magnetic Resonance in Medicine 36:588-595, 1996.
Dumoulin et al., Real-Time Position Monitoring of Invasive Devices . . . , Magnetic Resonance in Medicine 1993, 29: 411-415.
Hardy et al., Interactive Coronary MRI, Magnetic Resonance in Medicine 40:105-111, (1998).
Kerr et al., Real-Time Interactive MRI on a Conventional Scanner, Magnetic Resonance in Medicine 38:355-367, (1997).
Parsons, Inability to Reason About an Object's Orientation Using an Axis . . . , Journal of Experimental Psychology: Human Perception and Performance 21:1259-1277 (1995).
TPL Roberts et al., Remote Control of Catheter Tip Deflection . . . , Magnetic Resonance in Medicine, vol. 48, No. 6, Dec. 2002, p. 1091, vol. 48, No. 6.
Susil et al., Multifunctional Interventional Devices for MRI . . . , Magnetic Resonance in Medicine 47:594-600, (2002).
Ware, The Visual Computer, pp. 245-253, vol. 6, (1990).
ZHAI, Interaction in 3D Graphics, Computer Graphics 32:50-54 (1998).
ZHAI, Human Performance in Six Degrees of Freedom Input Control, Ph.D. Thesis, University of Toronto, (1995).

* cited by examiner

DEVICE AND PROCESS FOR MANIPULATING REAL AND VIRTUAL OBJECTS IN THREE-DIMENSIONAL SPACE

CROSS REFERENCE TO RELATED APPLICATIONS

Not Applicable.

FEDERAL SPONSORSHIP

Not Applicable.

BACKGROUND

1. Field of the Invention

The present invention relates to a six-degree-of-freedom mechanical armature and an integrated software system with input and output capability for manipulating real and virtual objects in three-dimensional space, and for manipulating a scan plane in magnetic resonance imaging.

2. Description of Related Art

Advances in medical imaging technology, including computerized tomography (CT), magnetic resonance imaging (MRI), and positron emission tomography (PET), coupled with developments in computer-based image processing and modeling capabilities, have lead to significant improvements in the ability to visualize anatomical structures in human patients. Real-time MRI inherently has advantages over conventional MRI because of its capability for rapid visualization of any scan plane and interactive adjustment of location. Interactive MRI is particularly useful for selecting an oblique scan plane in coronary artery cardiac imaging (see, for example, Hardy et al., *Magnetic Resonance in Medicine* 40:105-111, 1998), Real-time MRI also provides visualization of the dynamic process of anatomical motion, such as arrhythmic cardiac motion and peristalsis in the abdomen, without requiring any type of respiratory or cardiac monitoring. Real-time MRI has also been used to guide and monitor interventional procedures (see, for example, Cline et al., *Radiology* 194: 731-737, 1995; Susie et al., *Magnetic Resonance in Medicine* 47:594-600, 2002).

Development of a 6-DOF system for the manipulation and representation of a scan plane is closely linked with recent developments in real-time MRI. During real-time MRI, the operator frequently needs to prescribe the scan plane by a sequential translation and/or rotation of the current scan plane. Typically, a Cartesian coordinate is attached to the image plane with the origin of the coordinate system at the center of the image, x pointing to the right, y upward, and z out of the image plane towards the user. The location and orientation of the scan plane are relatively independent. The center of the field-of-view can be changed by sliding in the x, y, and z directions of the image plane while maintaining orientation of the scan plane. Alternatively, the scan plane can be rotated along any x, y, or z axis without necessarily changing its location. The operation of scan plane prescription is therefore essentially a 6-DOF task, which generally is difficult to perform because of the high dimensionality of the required operations. Human observers normally cannot mentally decompose orientation into separate rotation axes (see, for example, Parsons, *Journal of Experimental Psychology: Human Perception and Performance* 21:1259-1277 (1995).

Typically, a flat-screen is the only resource available to graphically indicate the location and orientation of the scan plane, compounding the problem of scan plane prescription. A two-dimensional projection of a wire-frame representation of the scan plane is often not enough to indicate its location and orientation. Considerable mental processing is required for the operator to adequately visualize the results of a sequence of translations and/or rotations of the scan plane. Operators often acknowledge the loss of awareness of the reference frame during real-time MRI. For example, it is well known in the art that an operator may incorrectly report a visual impression that the scan plane should go deeper in order to better capture a structure, when in fact the scan plane should actually be shallower. Moreover, the operator can only be certain that the last executed prescription is correct when the most recent magnetic resonance ("MR") image is displayed. This "try-and-see", trial-and-error approach is time consuming and often causes frustration for human operators.

In order to overcome the limitations noted above, interest has developed in the design of more intuitive user interfaces. However, most of this work focuses on software development to provide graphical tools (see, for example, Debbins et al., *Magnetic Resonance in Medicine* 36:588-595, 1996; Kerr et al., *Magnetic Resonance in Medicine* 38:355-367, 1997). State-of-the-art scan plane prescription is relatively time consuming. Using a standard mouse for pointing and clicking, a typical prescription of a double-oblique imaging plane using a commercial ID-rive interface (General Electric Medical Systems, Milwaukee) requires about 20 seconds. During clinical procedures, the precise placement of several scan planes is made even more difficult because of other ongoing time-limited demands experienced by the operator. For example, during stress echocardiography the operator must potentially record a number of dynamic imaging events, including changes in myocardial wall motion and tissue blood flow, during a period of transient tissue ischemia.

To improve the efficiency of scan plane prescription, hardware devices have been adopted for MRI applications (see, for example, Hardy et al. *Magnetic Resonance in Medicine* 40:105-111 (1998). Although some currently used hardware devices such as the Spaceball are capable of providing 6-DOF input, their usage is non-intuitive, primarily because the direction and distance of 3-D translation is controlled by the force vector that the operator exerts upon the sphere. Similarly, the rotation is controlled by the torque. Furthermore, current hardware devices provide inadequate visual feedback about the spatial location and orientation of the current scan plane. Consequently, the operator does not have adequate spatial awareness and often is left with an unacceptable level of uncertainty concerning the next moving direction. Spaceball is an isometric device which is good for rate control, but not good for position control (see, for example, Zhai *Computer Graphics* 32:50-54 (1998). Spacemouse might have some potential for providing 6-DOF input, however, it suffers the same problem as a Spaceball, namely it returns back to a null rest station when user support is withdrawn.

The prior art does not disclose a method or device that is capable of providing input 6-DOF spatial information while also physically representing the spatial location and orientation of the object after the manipulation, which is also capable of automatically changing its position and gesture to imitate its virtual correspondence. The integration of these capabilities is essential for the manipulation of a virtual object in 3D space. The present invention discloses a system wherein an input device provides 6-DOF spatial information which is integrated with an output device for efficient and intuitive scan plane prescription.

Comparison with Existing Devices

The best known and simplest implementation of 6-DOF manipulation is provided by the graphical sliders available on commercial computer screens. In the conventional method of MRI scan plane prescription, each slider is dragged with the standard computer mouse with 2-DOF with three sliders devoted to offset the next scan plane along x, y and z axes relative to the current plane, and another three for the rotation angles along x, y, and z axes. However, these conventional methods have fundamental problems. First, an operator can manipulate only one degree at a time, which makes it impossible to execute a coordinated movement in 6-DOF space. Second, human operators generally cannot mentally decompose orientation into separate rotation axes (see, for example, Zhai, *Computer Graphics* 32:50-54, 1998). Consequently, given a target orientation, an operator cannot determine the rotation angles along each rotation axis required to reach the goal without first executing several "practice" attempts blindly. Third, since each scan plane is prescribed relative to the previous scan plane, the axes for rotation are not static and evolve with time. This time-dependence feature makes scan plane prescription even more difficult than the operations involved in a fixed coordinate system. The present invention overcomes all of these problems by enabling the operator to move in a coordinated manner all 6-DOF required for the prescription of a scan plane.

Several prior art methods prescribe a double oblique scan plane using a mouse as an input device based on a multi-step procedure. Typically, in the first step of the procedure, two points placed on a current image plane are connected as a line which determines an orthogonal plane to the current plane, and serves as the intermediate scan plane. After an image is obtained in the intermediate scan plane, the first step in the procedure is repeated to obtain the final scan plane, which may or may not be the correct final scan plane. In this prior art method for scan plane prescription, additional corrective steps may be required to achieve the correct final scan plane. Moreover, this method does not allow the user to manipulate in a coordinated manner all degrees-of-freedom at the same time. In addition, this method relies on the flat screen to display the location and orientation of the scan plane in 3-dimensional space. It is well known in the art that a flat screen is not sufficient in the depth-dimension and often induces visual ambiguity. The present invention overcomes the first problem and solves the second one by providing a physical representation of the scan plane relative to the patient coordinate.

A mouse is usually classified as a free-moving isotonic device wherein displacement of the device is typically mapped to a cursor displacement. An isometric device, by comparison, does not move but rather remains fixed relative to a desktop. In general, an isotonic device provides superior performance for positioning tasks compared to an isometric device (see, for example, Zhai, *Computer Graphics* 32:50-54, 1998).

Modifications to a standard mouse are known in the prior art which make it possible to input the third coordinate as well as incorporate 3-D rotations (see, for example, the "Bat" device disclosed by Ware, The Visual Computer, Vol. 6, pp 245-253, 1990). U.S. Pat. No. 5,503,040 to Wright discloses a computer interface device now commercially available as "Cricket"™ (Digital Image Design Inc New York http://www.didi.com/www/areas/products/cricket/ which includes a gimbal mounted handle having a plurality of input members for effectively communicating navigation and command signals to a computer. This invention provides an operator with 6-DOF for navigation within a virtual reality world while simultaneously enabling the operator to enter a series of commands in order to effectively communicate the operator's intentions to a computer to effect a change within a virtual reality world. Similarly, the MITS Glove™ designed by Zhai (Zhai, Human Performance in Six Degrees of Freedom Input Control, Ph.D. Thesis, University of Toronto, 1995) provides 6-DOF input control.

However, most of these modified high-dimensional "flying mice" are instrumented with a magnetic tracker for 6-DOF sensing, which makes them inaccurate in the environment of MRI. Another drawback is that the devices cannot remain at a particular location without support, which makes its difficult to resume an incomplete operation due to either fatigue or re-positioning of the hand.

U.S. Pat. Nos. 5,335,557, 5,729,249, and 5,805,137 issued to Yasutake disclose touch sensitive input control isometric devices that are now available commercially ("Spaceball"™, Spaceball Technologies.) These patented devices provide a family of controllers which incorporate multiple force/touch sensitive input elements to provide intuitive input in up to 6-DOF, including position and rotation, in Cartesian, cylindrical, or spherical coordinate systems. Six dimensions of input can be generated without requiring movement of the controller, which provides a controller suitable for controlling cursors and display objects in an interactive computer system. Positional information is obtained either by use of a "pushing" or "dragging" metaphor. Rotational information is provided by either a "pushing," "twisting," or "gesture" metaphor. The same sensor is used for both positional and rotational inputs, and the two are differentiated by the magnitude of the force applied to the sensor.

Spaceball™ devices have been used to prescribe the scan plane of MRI (see, for example, Hardy et al., *Magnetic Resonance in Medicine* 40:105-111, 1998). The scan plane is rotated on any axis by twisting the sphere around that axis and is translated in any direction by pushing the sphere in that direction. An alternative user interface strategy is provided by the multi-axis hand controller disclosed by U.S. Pat. No. 6,101,893 to Wergen, now marketed as "Spacemouse"™ by Logitech U.S.A. "Spacemouse"™ is an elastic device with a small range of movement (5 mm in translation and 4 degree in rotation). A multidimensional handle controlled without displacement is used for precisely positioned control and input. The actuating rod is selectively and simultaneously subjected to lateral pressure and to bending by a surrounding fist. The third dimension is controlled without displacement by the thumb, which acts on an additional sensor lever.

There are, however, significant limitations to the inventions embodied by "Spaceball"™ and "Spacemouse"™, including insufficient feedback to the user at the kinesthetic channel (see, for example, Zhai, *Computer Graphics* 32:50-54, 1998). For example, Spaceball™ is completely rigid, which presents a serious limitation because kinesthetic or proprioceptive feedback can be critical to the operator's control performance. A second limitation of Spaceball™ is that it returns to a null-position when released giving no feedback on the current location in 3-D space of the object under manipulation. The 6-DOF system disclosed by the present invention overcomes these problems by being more intuitive in manipulating the scan plane. In the method of the present invention, the armature device is capable of maintaining the current location and orientation of the scan plane to provide better spatial awareness for the operator. In addition, the armature device can be used according to the invention to automatically place the surface to reflect the prescribed virtual scan plane.

6-DOF Devices in the Prior Art

Exemplary of other multi-degree devices is the finger manipulable 6-DOF "Fingerball"™ input device disclosed in U.S. Pat. No. 5,923,318 to Zhai et al. "Fingerball"™ is a 6-DOF isotonic device that an operator holds and freely moves in real 3-D space to control the position and orientation of a virtual 3-D object. Zhai's invention provides an isotonic 6-DOF input device which includes a housing having a shape and dimension effective to permit an operator to grasp and manipulate the housing using the fingers of one hand. In one embodiment the housing encloses an interior cavity adapted to contain a position sensor. The entire housing is a pressure sensitive switch which is activated by the operator squeezing the housing with his fingers and/or thumb from any position on the outer surface of the housing. In a preferred embodiment the input control device is spherical in shape and has a textured outer surface adapted to prevent slippage in the operator's fingers. In addition to the large muscle groups of the shoulders, arm and hand, the input device makes extensive use of the small muscle groups of the fingers and thumb. However, unlike the present invention, the "Fingerball"™ device disclosed by Zhai et al. is not able to maintain its position when support is not provided.

U.S. Pat. No. 6,115,028 issued to Balakrishnan et al. discloses a device for the input of 3 spatial coordinates. Balakrishnan's invention provides a three dimensional input system using tilt, an input system for controlling the position or motion of a cursor, and three dimensions that use x, y, and z positions for inputting two coordinates and tilt in a plane (x-y or z-y) to input a third (and possibly a fourth coordinate). The input system disclosed in Balakrishnan et al. for controlling the position or motion of a cursor. The controlled cursor is moved about on a surface for inputting two of the dimensions and tilted to input the third. The amount or degree of tilt and the direction of tilt controls the input of the third dimension. The base of the hand held device is curved so that the device can be tilted even while it is moved in two dimensions along the surface of the tablet. Tilting can be along two orthogonal axes allowing the device to input four coordinates if desired. The coil can also have switched resistors controlled by mouse buttons connected to it which the tablet can sense being activated to allow clutching and selection operations like those of a conventional mouse. Although the "MicroScribe 3D digitizer"™ can simultaneously provide 6-DOF inputs, unlike the present invention it cannot statically maintain its position or orientation. Furthermore, unlike the mechanical armature device disclosed by the present invention, the "MicroScribe 3D digitizer"™ cannot be used as an output device to generate a physical representation of the position/orientation of a virtual object. Other examples of mechanical armature devices with 6-DOF include several force-feedback hand controllers that are capable of inputting spatial coordinate/orientation information and output force feedback. These devices are available commercially as "Freedom 6S Force Feedback Hand Controller"™ (MPB, Montreal, Canada) and "Phantom 6-DOF"™ (SenSable Technologies, USA).

U.S. Pat. No. 5,576,727 issued to Rosenberg et al. discloses an electromechanical human-computer interface with force feedback method and apparatus, which can provide commands to a computer through tracked manual gestures and also provide feedback to the operator through forces applied to the interface. The invention disclosed by Rosenberg et al. provides an operator manipulable object coupled to a mechanical linkage that is, in turn, supportable on a fixed surface. The mechanical linkage or the operator manipulable object is tracked by sensors for sensing the location and/or orientation of the object. A multi-processor system architecture provides a host computer system interfaced with a dedicated microprocessor that is responsive to the output of the sensors and provides the host computer with information derived from the sensors. The host computer has an application program which responds to the information provided via the microprocessor and which can provide force-feedback commands back to the microprocessor. The force feedback is felt by an operator via the user manipulable object. Although the invention disclosed by Rosenberg et al. provides 5- or 6-DOF force feedback control with the feature of static balance, it is distinguished from the present invention by the fact that it is incapable of automatically moving to a given position with a desirable orientation. In addition, not all of its joints can maintain balance.

U.S. Pat. No. 6,593,907 issued to Demers et al. discloses a tendon-driven serial distal mechanism for providing 3-DOF for a rotating handle. According to this invention, three stages provide a serial mechanical linkage between a handle and a platform, which may itself be moveable in three degrees of freedom. Each stage has an axis of rotation, and the three axes intersect. The first stage is mounted to the platform in such a way as to provide rotation about the first stage axis. The first stage carries the second, allowing the second stage to rotate about its axis. The second stage carries the third stage, allowing the third stage to rotate about its axis. The third stage is fixed to the handle, and the third stage axis passes along the length of the handle. Each stage has a sensor to measure its rotation, and a tendon means of transferring torque from a remote motor to torque about the rotation axis of the respective stage. The sensors have two limited angle ranges of measurement, about 110 degrees wide and on opposite sides of the rotation. The third stage has an auxiliary sensor, mounted in quadrature to the main third stage sensor and connected to an idler that carries the third stage tendon. The auxiliary third stage sensor measures angles of rotation that are not measured by the main third stage sensor. The two third stage sensors together provide continuous roll measurement about the third stage axis. However, unlike the present invention, the device invented by Demers et al. does not represent the position/orientation of the corresponding virtual object. Furthermore, unlike the present invention, the method disclosed by Demers et al. is not able to automatically position a real object in the real world.

U.S. Pat. No. 5,792,135 issued to Madhani et al. discloses an articulated surgical instrument for enhancing the performance of minimally invasive surgical procedures. The instrument has a high degree of dexterity, low friction, low inertia and good force reflection. A cable and pulley drive system operates to reduce friction and enhance force reflection, and a wrist mechanism operates to enhance surgical dexterity compared to standard laparoscopic instruments. The system is optimized to reduce the number of actuators required and thus produce a fully functional articulated surgical instrument of minimum size. The four actuators are coupled by the four cables to the wrist mechanism, the rotary joint and the linear joint such that selective actuation of the actuators operates to move the first work member of the surgical end effector about two orthogonal axes with two degrees-of-freedom relative to the support member, extend and retract the support member along the support axis relative to the support bracket and rotate the support member about the support axis relative to the support bracket and thereby move the first work member of the surgical end effector relative to the support bracket with four degrees-of-freedom.

U.S. Pat. No. 6,394,998 issued to Wallace et al. discloses surgical instruments for use in minimally invasive telesurgical applications. The instruments include a base whereby the instrument is removably mountable on a robotically controlled articulated arm. An elongate shaft extends from the base. A working end of the shaft is disposed at an end of the shaft remote from the base. A wrist member is pivotally mounted on the working end. At least one end effector element mounting formation is pivotally mounted on an opposed end of the wrist member. A plurality of elongate elements, e.g., cables, extend from the end effector element mounting formation and the wrist member to cause selective angular displacement of the wrist member and end effector mounting formation in response to selective pulling of the elongate elements.

U.S. Pat. No. 6,441,577 issued to Blumenkranz et al. discloses techniques and structures for aligning robotic elements with an internal surgical site and each other. Manually positionable linkages support surgical instruments. These linkages maintain a fixed configuration until a brake system is released. While the brake is held in a released mode, the linkage allows the operating room personnel to manually move the linkage into alignment with the surgical site. Joints of the linkage translate the surgical instrument in three dimensions, and orient the surgical instrument about three axes of rotation. Sensors coupled to the joints allow a processor to perform coordinate transformations that can align displayed movements of robotically actuated surgical end effectors with a surgeon's hand inputs at a control station.

Applications to MRI

Motion artifacts due to normal or abnormal respiratory movements can degrade image quality in MR scans. Motion artifact suppression techniques have been useful in coronary artery imaging and in monitoring of heart wall motion, which is useful to assess the severity and extent of damage in ischemic heart disease. MR imaging of the coronary arteries, or MR angiography (MRA), has typically been performed using a technique to limit the MRI acquisition to avoid motion artifacts. Such techniques include requiring the patient to withhold breathing during the imaging, using oblique single-sliced image techniques, or respiratory-gated 3-D imaging techniques. However, repeated breath holding may not be feasible for many coronary patients and navigation techniques to-date have not generally provided a robust method which works over a range of different breathing patterns in a variety of patients. Another drawback to these approaches is that success or failure is usually not apparent for some time after the start of imaging, and many times not until the imaging has been completed.

Another application of the scan plane and image navigation method disclosed by the present invention relates to myocardial perfusion imaging to detect the passage of a contrast agent through muscle tissue in the heart and to study blood flow in the micro-circulation of the heart non-invasively. Typically, perfusion imaging consists of using injected contrast agents together with rapid imaging during the first pass of the contrast agent through the microvasculature with carefully optimized pulse-sequence parameters. Quantification of blood flow from these images is carried out with a region of interest-based signal, time-intensity curve analysis. To avoid cardiac motion artifacts, the perfusion images are typically acquired with ECG gating. However, since the period of image acquisition is usually one to two minutes long, the images suffer from significant respiratory motion artifacts. This then requires a manual registration and analysis of the perfusion images, which is cumbersome and time-consuming because the user must carefully arrange each image to compensate for the respiratory motion before proceeding to a region of interest time-intensity analysis.

A key requirement in minimally invasive procedures is to integrate the positioning of instruments, needles, or probes with image guidance to confirm that the trajectory or location is as safe as possible, and to provide images that enhance the ability of the physician to distinguish between normal and abnormal tissues. In interventional MRI applications, instruments must be positioned accurately within the field of view (FOV) or near the FOV of image acquisition. Placement may require acquisition of static images for planning purposes, either in a prior MRI examination or during the interventional MRI session, or real-time images in arbitrary scan planes during the positioning process. (See, for example, Daniel et al. SMRM Abstr. 1997, p. 1928; Bornert et al. SMRM Abstr. 1997, p. 1925; Dumoulin et al., Mag. Reson. Med. 1993, 29: 411-415; Ackerman et al., SMRM Abstr. 1986, p. 1131; Coutts et al., Magnetic Resonance in Medicine 1998, 40:908-13. One useful application of the present invention is to manipulate a virtual or real 3-D object, such as, for example, an ultrasound transducer to a position and rotate it to a desirable orientation corresponding to an MR scan plane position. Examples of other interventional MRI procedures that would benefit from the present invention include image-guided interstitial probe placement to provide high-temperature thermal therapy, cryotherapy, or drug therapy for tumors; localization of non-invasive focused ultrasound probes below the tissue surface for thermal therapy; and subcutaneous or transdural placement of biopsy needles or surgical instruments for minimally-invasive surgery.

For interventional MRI applications, there is the additional need to register data from other imaging modalities to provide comprehensive and complementary anatomical and functional information about the tissue of interest. Registration is performed either to enable different images to be overlaid, or to ensure that images acquired in different spatial formats (e.g., MRI, conventional x-ray imaging, ultrasonic imaging) can be used to visualize anatomy or pathology in precisely the same spatial location. While some algorithms exist for performing such registrations, computational cost would be significantly reduced by developing technology that enables data from multiple different imaging modalities to be inherently registered by measuring the patient's orientation in each image with respect to a common coordinate system.

SUMMARY OF THE INVENTION

The present invention discloses an integrated system comprising software and hardware, wherein a mechanical armature integrated with software provides both input and output capability for manipulating real and virtual objects in 3-dimensional (3D) space. The mechanical armature provides six degree-of-freedom ("6 DOF") object manipulation and representation. One primary function of the armature device is to generate a physical representation of a 2-dimensional scan plane of a magnetic resonance image relative to an object in real patient coordinates.

The invention comprises a series of mechanical linkages connected by rotational joints to a planar surface with a stylus perpendicular to the surface. Manipulation of the stylus will also move the attached planar surface. The surface can represent an imaging plane.

In the input mode, the operator manually moves the stylus to a physical location in three-dimensional space, and also manually adjusts the orientation of the stylus. Each rotational joint of the armature contains a sensor/encoder that relays the rotation and location of each rotational joint to the computer. In the input mode, the software system uses the information provided from the sensor/encoders and forward kinematics to calculate and provide the x, y, and z location, and pitch, yaw, and roll rotational values. The 3D location and orientation of the stylus and surface can then be represented on the 2D computer screen.

In the output mode, the operator programs a location and orientation of the planar surface into the computer. This location and orientation can be arranged into a 4×4 geometrical matrix. Using inverse kinematics, the computer can calculate the corresponding angular positions for the six joints of the armature. Then the motor located at each rotational joint will drive the corresponding linkage to rotate until the reading of the joint's encoder/sensor has indicated that the target position has achieved. Therefore, the surface and the attached stylus move automatically to the target location with the desired orientation.

In the output mode, the software system allows the operator to program the computer using sliders, or a combination of sliders and buttons, or any other software based graphical user interfaces.

The operator can use the software system to program subsequent imaging planes based on the current image plane. The surface contained in the 6-DOF mechanical armature can move automatically to reflect the effects of the operator's action, thereby providing the operator spatial awareness in order to quickly localize the optimal scan plane. In the output mode, the software system uses inverse kinematics to automatically move the surface and stylus to a specific position and orientation, thereby providing a physical representation of virtual 3D information shown on the computer screen.

In either mode, the information concerning the physical location and orientation of the surface and stylus is transmitted to the computer via a sensor/encoder. In either mode, the planar surface of the invention gives the operator a clear indication of the location and orientation of the current scan plane relative to a reference coordinate that is fixed on a real patient.

The armature device is capable of statically maintaining its position and orientation. The resulting spatial awareness enables the operator to anticipate and better appreciate the direction of the next movement, thereby enabling improved visualization of the object under investigation.

The invention has specific applications in MRI. Using the armature in its input mode, the operator may command a magnetic resonance scanner by inputting the spatial location and orientation of the scan plane relative to a patient in the real world.

The operator may also program the system to constrain the changes in scan plane position and orientation to a pre-specified range when desirable (e.g. when one wants to move the scan plane in a direction perpendicular to the current plane or shift location within the same plane).

These features enable the operator to move in a coordinated manner all 6-DOF required for the optimal scan plane. The capability for surface manipulation in three-dimensional space disclosed by the present invention can also be used for image navigation based on spatial information from a 4×4 matrix contained in the header file of each image. It is also ideal for the automatic manipulation of a medical device including, for example, an ultrasound transducer, to a given position indicated by three spatial coordinates and to rotate said medical device to a given orientation indicated by a 3×3 rotation matrix, provided for example by a medical image.

In the method of the invention, software provides graphical visual information about the object being imaged, the projected display of the 2-dimensional scan plane, and the expected MRI image corresponding to that scan plane of the tissue being imaged. According to the invention, software also provides a user interface for the control of the magnetic resonance scanner and the 6-DOF hardware, as well as the driver and algorithms that relate to the 6-DOF device.

One aspect of this invention is to provide an integrated input and output device for the control of a virtual or real 3-D object.

A second aspect of the present invention is to provide an integrated input and output system for the control of a 2-D plane in virtual or real 3-D space.

Another aspect of the present invention is to provide an integrated input and output system, wherein said input device provides 6-DOF spatial information for efficient and intuitive scan plan prescription and said output device provides automatic tracking and physical representation of the scan plane Another aspect of the present invention is to facilitate application of constraints to the allowed range of changes in position and/or orientation of the object under manipulation.

Yet another aspect of this invention is to provide an integrated input and output system for the control of a scan plane in magnetic resonance imaging.

A further aspect of this invention is to provide an armature and software system for interventional MRI applications wherein images are used to guide and monitor minimally invasive diagnostic and therapeutic procedures.

Another aspect of the present invention is to provide an integrated input and output system for applications that require accurate registration of MRI data with data obtained using other imaging modalities.

Yet another aspect of this invention is to provide a device and method for detecting and tracking positional changes in a reference structure that is computationally efficient.

Another aspect of this invention is to provide a system and method that is not reliant on operator input or influence during an MRI procedure.

A further aspect of the present invention is to provide a method and device for 6-DOF surface manipulation and representation whose function is independent of the MR scanner Another aspect of this invention is to provide a system for 6-DOF object manipulation and representation, wherein the position of anatomic structures in a human body can be accurately detected in magnetic resonance images.

Yet another aspect of the present invention to provide a system for 6-DOF surface manipulation and representation, which enables MR imaging with the same spatial location and orientation in different examinations.

Still another aspect of this invention is to provide a system to validate image-based co-registration algorithms.

Another aspect of the present invention is to provide a system for 6-DOF surface manipulation and representation which is useful for both conventional clinical MRI and functional MRI studies.

A further aspect of this invention is to provide an armature and software system for surface manipulation in three-dimensional space, which is useful for image navigation based on spatial information.

Yet another aspect of the present invention is to provide an armature and software system under real-time computer control to support an interventional treatment system for use with surgical tools and tissue manipulators.

A further aspect of this invention is to provide an armature and software system under real-time computer control to support interventional treatment procedures, including in vivo delivery of drugs, angioplasty devices, biopsy and sampling devices.

Another aspect of this invention is to provide an armature and software system under real-time computer control to guide interventional devices, which deliver RF, thermal, microwave or laser energy or ionizing radiation.

A further aspect of the present invention is to provide an armature and software system under real-time computer control to support internal illumination and imaging devices, such as catheters, endoscopes, laparoscopes, and similar instruments.

These and other features, objects, and advantages of the present invention will be obvious upon consideration of the following detailed description of the invention. It will also be apparent to those of ordinary skill in the art that many changes and modifications may be made without departing from the scope of this invention.

DETAILED DESCRIPTION OF THE INVENTION

Figure 1:
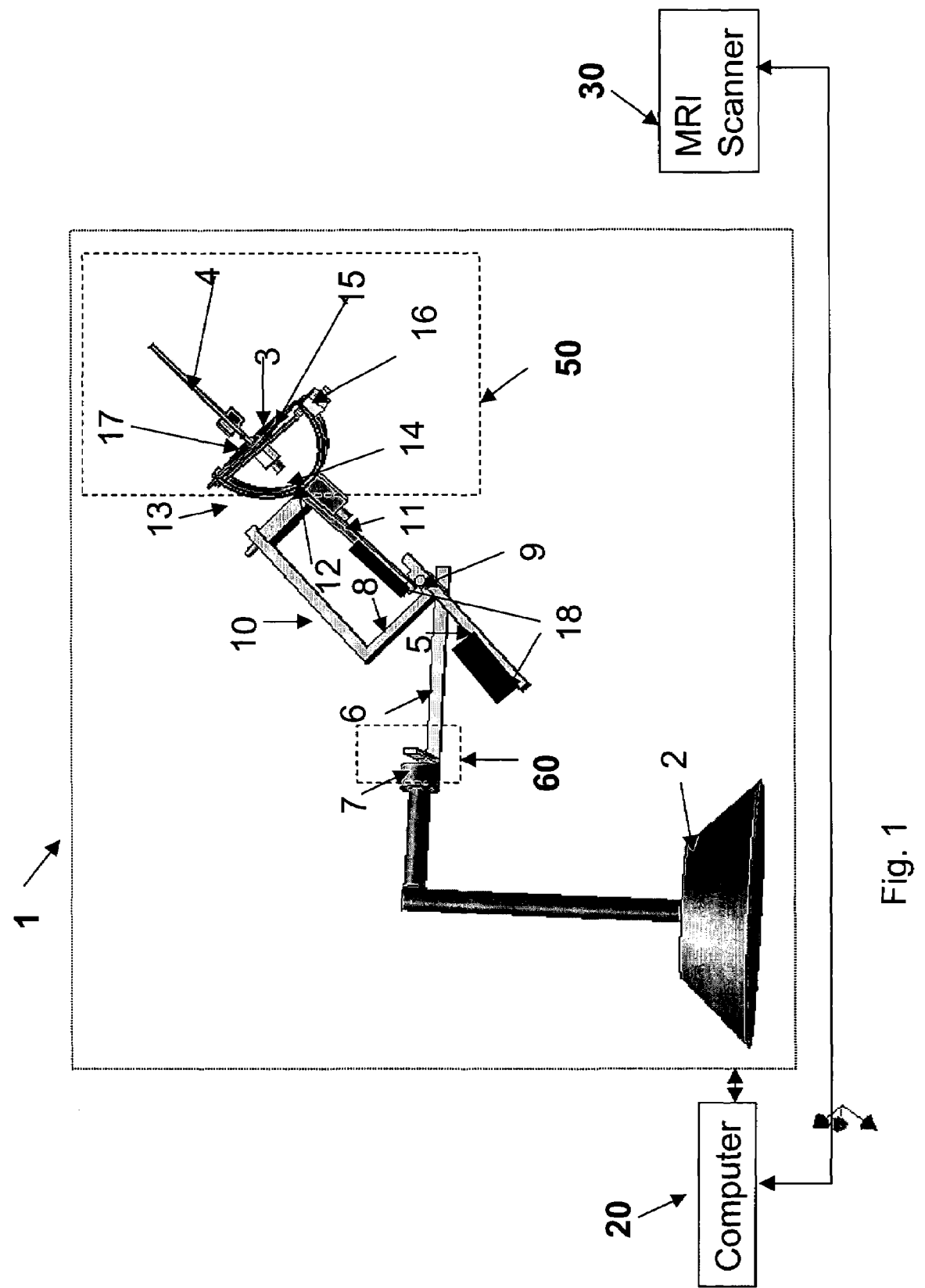
FIG. 1 is a side view of the mechanical armature disclosed by the present invention.

With reference to FIG. 1 of the drawings, the 6-DOF hardware disclosed by the present invention is a mechanical armature 1 consisting of six mechanical linkages that support a surface 3, and a pencil-like stylus 4 fixed to the center of the surface 3 to serve as a line perpendicular to the surface, i.e., the normal surface. In one preferred embodiment of the invention, the first linkage 6 is connected to a fixed base 2 through the first rotational joint 7 such that the first linkage can rotate along its longitudinal axis. The base 2 can be removably or permanently fixed to any one of a number of surfaces, including the surface of a desk. According to the invention, the second linkage 8 is connected to and supported by the first linkage 6 at the second rotational joint 9 and can rotate along an axis that is perpendicular to the first mechanical linkage 6. The rotation axes of the first joint 7 and the second joint 9 are perpendicular at any point in time. The third linkage 10 is connected to and supported by the second mechanical linkage 8 and is fixed relative to the second linkage 8. According to the invention, the fourth linkage 11 is connected to and supported by the third linkage 10 at the third rotational joint 12. Fourth linkage 11 is able to rotate along an axis that is perpendicular to the third linkage. The rotation axes of the second joint 9 and the third joint 12 are perpendicular at any point in time. In the method of the invention, the fifth linkage 13 is a half circle. Its middle point is connected to and supported by the fourth linkage 11 at the fourth rotational joint 14. Fifth linkage 13 is able to rotate along a diameter that is passing through its center and its middle point. The sixth mechanical linkage 15 is connected with its two ends to, and supported by the fifth linkage 13. Both ends of the linkage 15 are rotatable, but only one is motorized and is regarded as the fifth rotational joint 16. The axis of rotation of sixth mechanical linkage 15 is a diameter of fifth linkage 13, running from fifth rotational joint 16 to the other end of linkage 15.

The surface 3 is connected to the sixth linkage 15 at the sixth rotational joint 17 and can rotate along a stylus 4 that is perpendicular to the sixth linkage 15. In the method of the invention, the stylus 4 is fixed to the center of and is perpendicular to the surface 3.

Weight balancing blocks 18 of heavy material such as lead are used as counter-balance so that the surface 3 and the stylus 4 can maintain their position and orientation at any point in temporal and spatial domains. Weight balancing blocks 18 are fixed to balance arm 5 and mechanical linkage 11.

The ability of the armature to maintain static balance is an essential part of the invention. Static balance is necessary to maintain the current position and orientation of the object under manipulation. Static balance is achieved by the combination of symmetric design, lightweight materials, friction, holding torque of motors 80, and where applicable, blocks 18.

According to the invention, mechanical leverage, friction, and counter-weight blocks 18 are used to support the stylus 4, which reduces the potential fatigue experienced with isotonic 3-D input devices such as a flying mouse. Hence, one benefit of the present invention is to enable the operator to freely move the stylus 4 and the attached surface 3 in 3-D space. The static nature of the armature device provided by the present invention enhances the stability and dexterity of the user manipulation of the stylus 4. According to the invention, with this support and the gears contained in the servo 19 used at each joint of the mechanical linkage, the stylus 4 and its surface 3 can remain static without direct operator support instead of drifting away or collapsing to a rest position when the operator releases the stylus 4.

Figure 2:
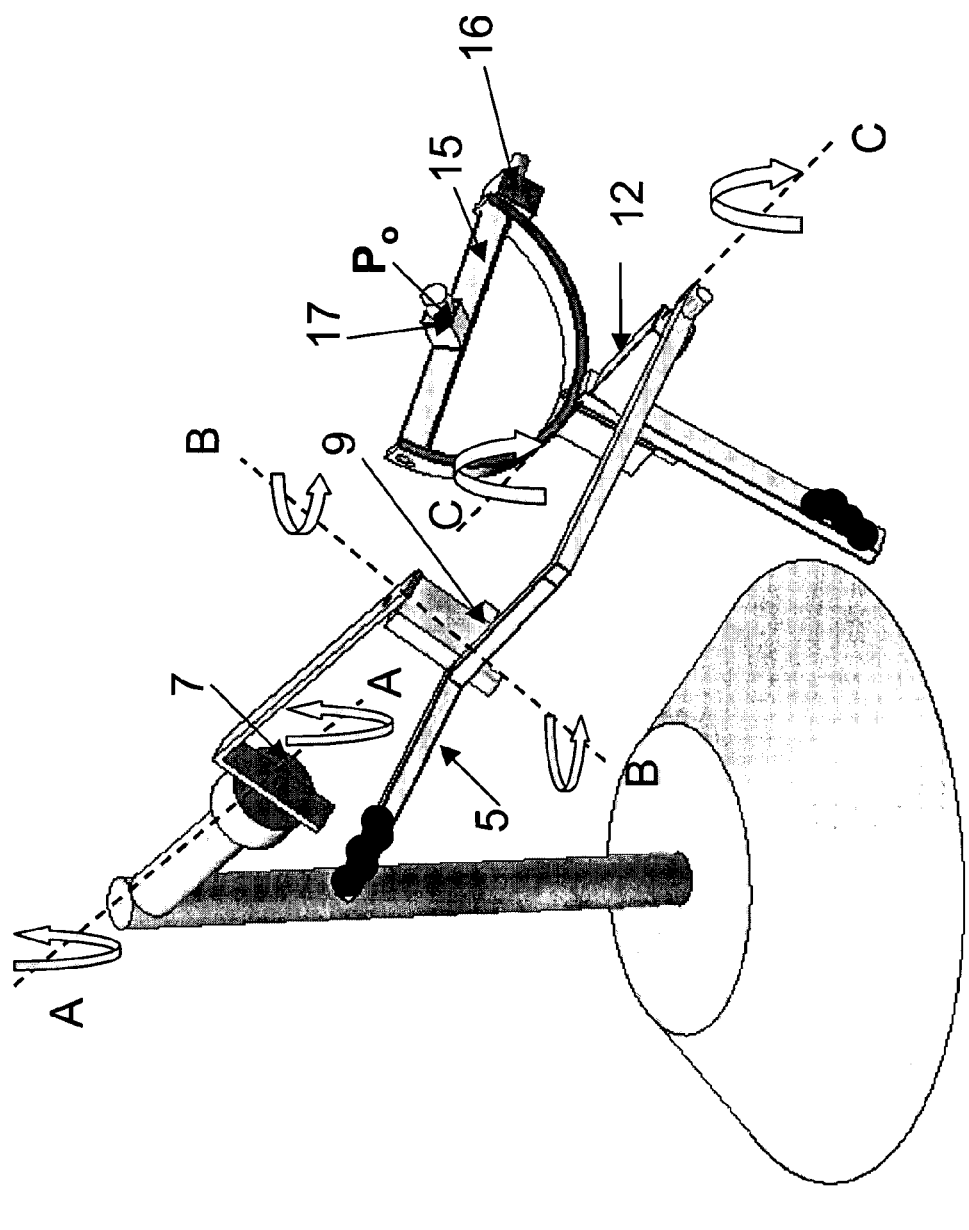
FIG. 2 is an oblique view of the mechanical armature.

FIG. 2 illustrates the first movement of the three rotation joints 7, 9 and 12 and their related linkages in more detail. According to the invention, the length of linkage 6, 8, 10, 11 and 13 can vary under a constraint such that the distance between joints 9 and 12 will be equal to the distance between joints 12 and 17. When the other joints are fixed, and only joint 12 is in effect, the center point $P_o$ of surface 3 will sweep along the axis C-C and produce a circle centered at the center of joint 12. However, since joint 12 is not fixed but can rotate along the axis B-B and results in another circle centered at the center of joint 9. When the distance between joints 9 and 12, and the distance between joints 12 and 17 are equal, the ultimate result of such rotation along different axes is a disk with a radius equal to twice the length between joint 9 and 12. According to the invention, this disk can rotate along axis A-A and result in a sphere centered at the center of joint 9, with a radius equal to twice the distance between joints 9 and 12. This sphere is the space that the center point $P_o$ can reach, or the work space of the mechanical armature. This indicates that the position of $P_o$ is only determined by the first three joints and is independent of the angular positions at joints 14, 16 and 17.

Figure 3:
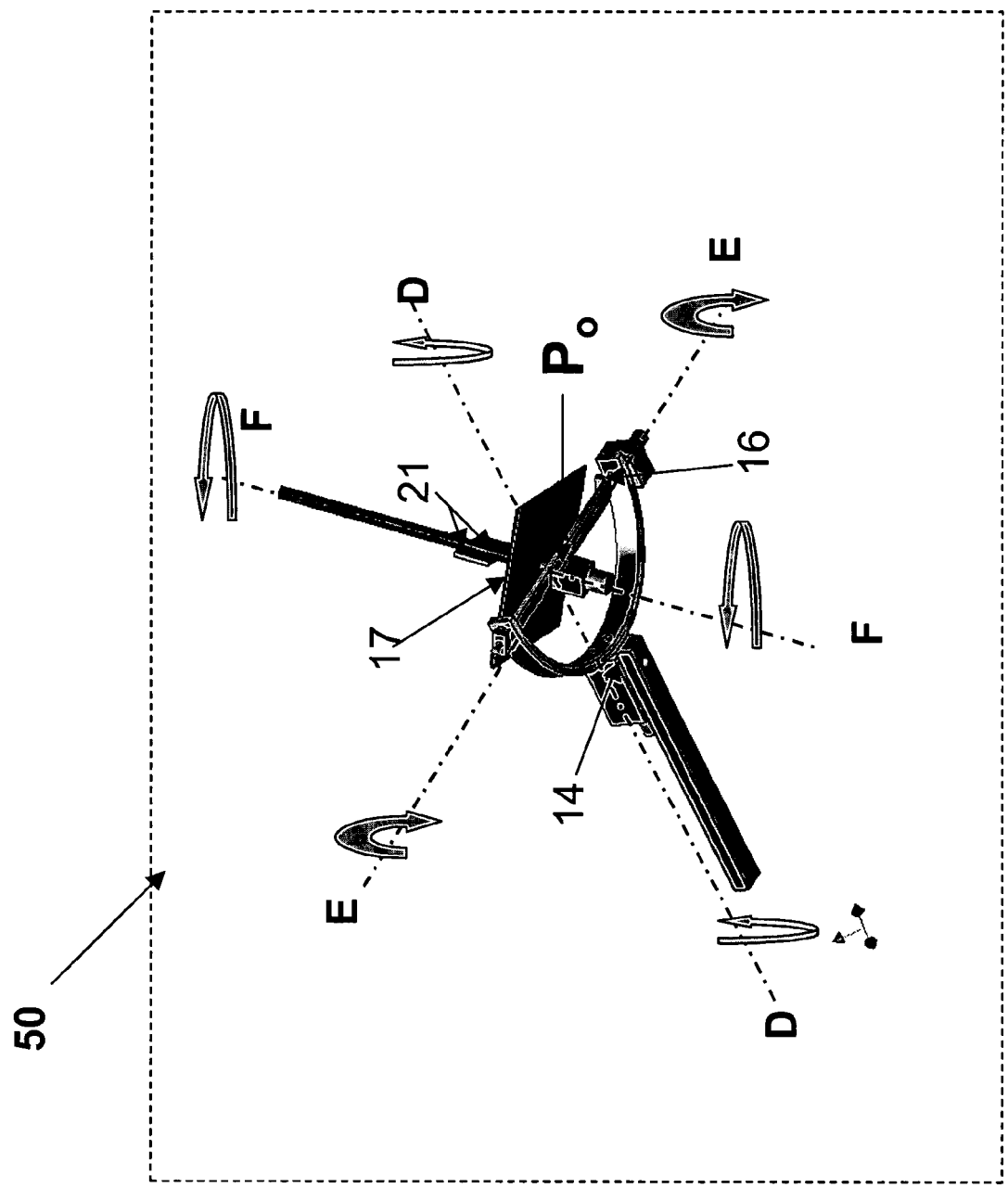
FIG. 3 is an enlarged view of area 50 shown in FIG. 1.

FIG. 3 illustrates in more detail the arrangement of the last three joints and corresponding rotational axis according to the present invention. Axes D-D, E-E and F-F cross at a single point, the center point $P_o$ of surface 3. In this way, the position of $P_o$ is completely independent of the angular positions of joints 14, 16 and 17.

The proximal end of linkage 4 has two ears 21 to allow the user to easily rotate the surface 3.

Figure 4:
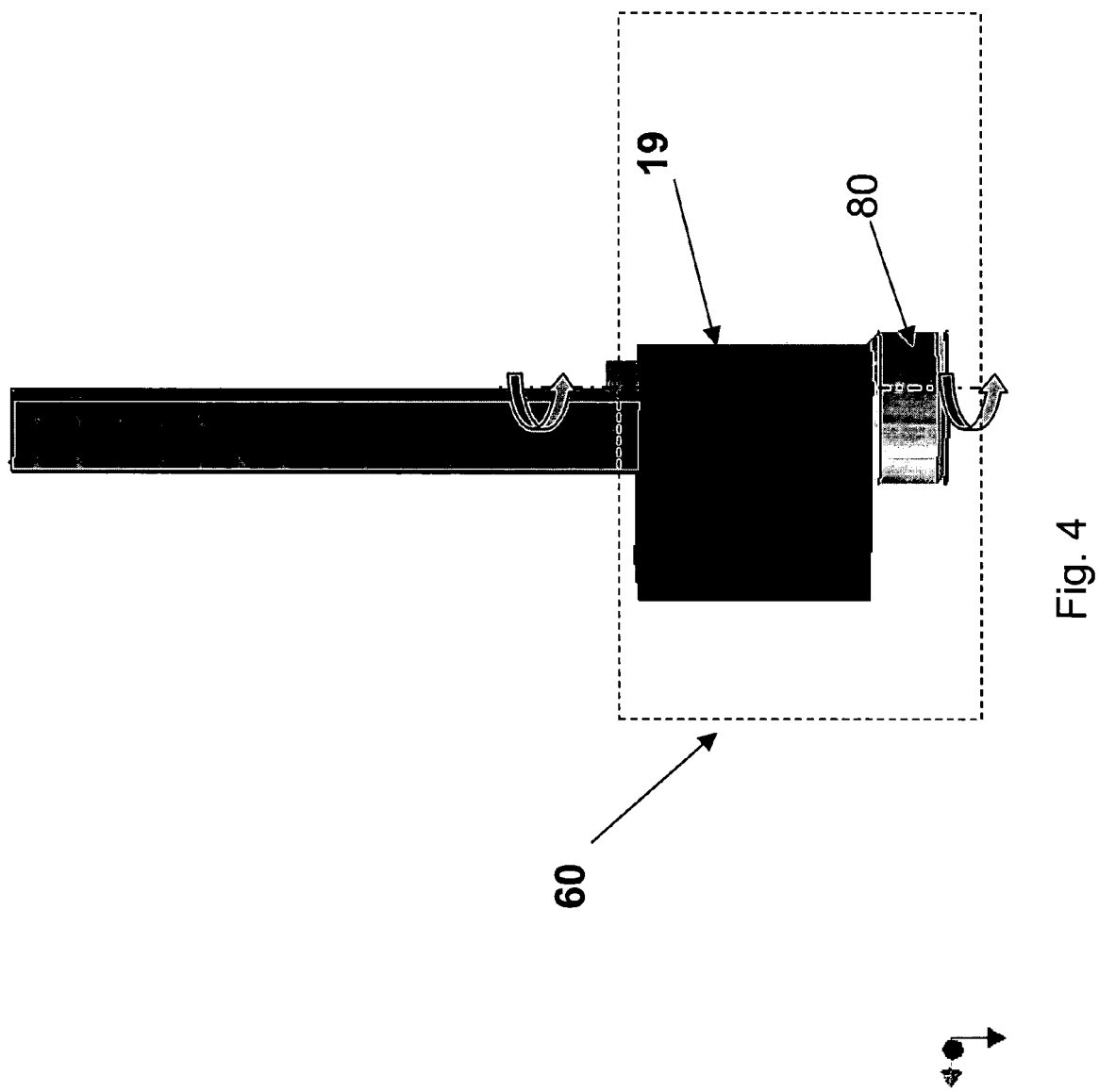
FIG. 4 is an enlarged view of area 60 shown in FIG. 1, and illustrates how each rotational joint between two linkages in the mechanical armature is coupled with a sensor and a motor.

FIG. 4 shows a close-up view of the sensor/encoder 80 coupled to motor/servo 19, located at each rotational joint between two linkages. The coupled sensor/encoder 80 and motor/servo 19 provide information about the angular position of each rotational joint. Sensor/encoder 80 may be either an optical encoder, a potentiometer, or some other mechanism for locating the position of an object in space. The information regarding the position of each rotational joint is transmitted from each sensor/encoder 80 via wires to the computer 20.

Using the known length of each mechanical linkage, the configuration of rotational axis of each joint, and readings of sensor/encoder 80 at each joint, the software can, using forward kinematic equations, calculate the position and orientation of the surface 3 and stylus 4 at any time point of normal operation. The resulting data yields a 4×4 matrix containing sufficient information to determine the position and orientation of a scan plane, which can be sent to command the MR scanner 30. The resulting scan plane is also displayed relative to the volume image of the object under investigation on a common computer screen. In the method of the invention, the expected image corresponding to the scan plane is also routinely displayed to the operator.

With further reference to FIG. 4, each joint between two linkages is coupled with a motor or servo 19. In one preferred embodiment, all motors are custom modified servos by Hitech which can be directly controlled by a common personal computer 20 through a parallel port supplied with simple linear DC power that avoids the high costs generally associated with multi-degree motor control. Each joint can rotate close to 360 degrees in order maximize workspace. In the practice of the invention, to concretely represent the scan plane by the device requires only a 4×4 matrix with the last column containing the three coordinates and the first three columns containing the orientation of the scan plane. According to the invention, this spatial information, the known length of each mechanical linkage, and the series of rotational axes are used by the software in the inverse kinematic equations needed to calculate the set of angles for the joints. Further in the method of the invention, these angles and the current angular locations of the joints are then used to rotate each linkage so that that the surface 3 is moved to a place to reflect the scan plane relative to a reference coordinate fixed on the object that is under investigation.

Figure 5:
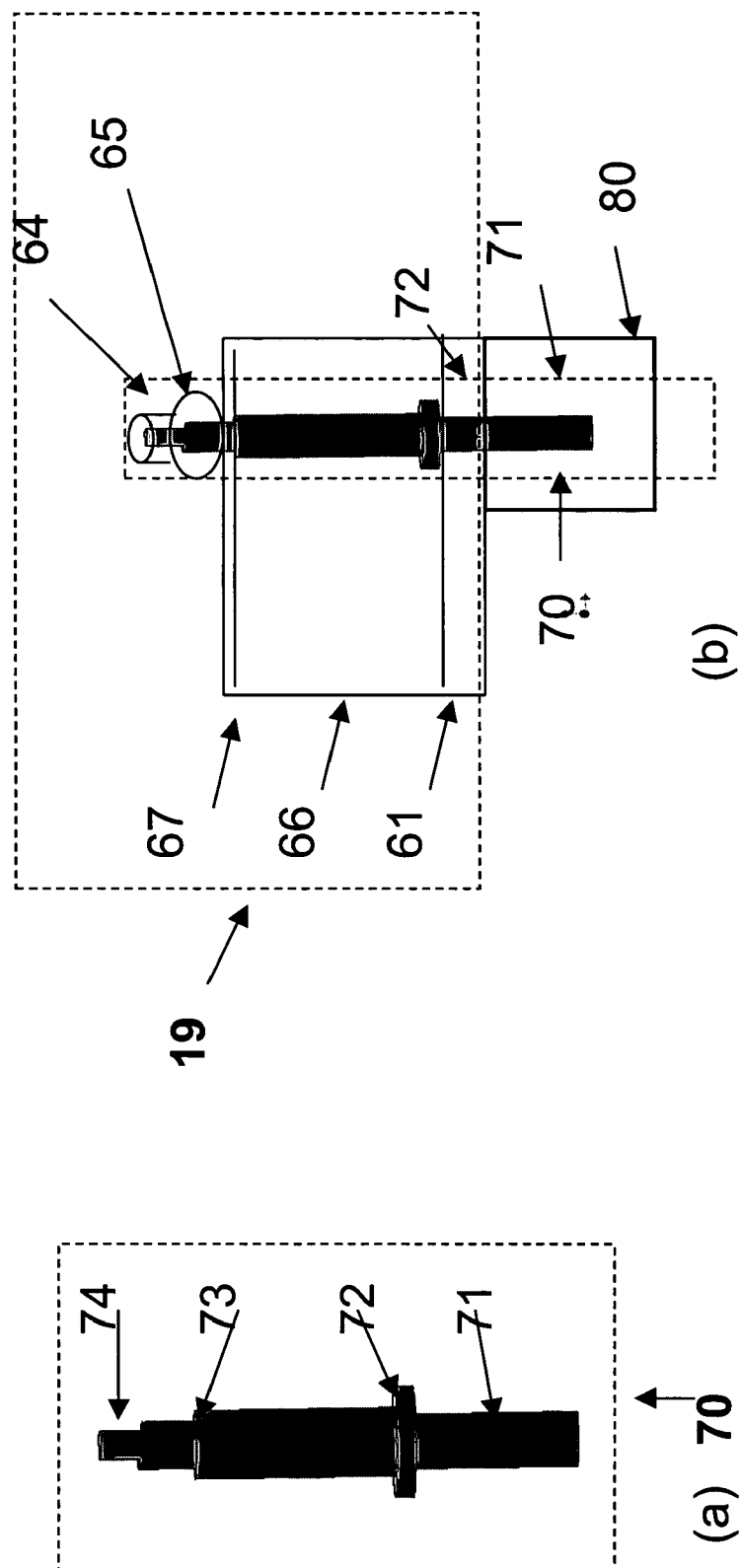
FIG. 5 gives a detailed example of how the servo is modified and coupled with an optical encoder.

With reference to FIG. 5, the servo/motor 19 and encoder/sensor 80 are coupled. The inventors have modified a standard servo/motor for use with the armature. The modification consists of removing the potentiometer of a standard servo/motor, on top of which the output gear 65 of the original servo sits. A mechanical adapter shaft 70 is used to mount the output gear 65 and transmit the rotational position of the servo/motor 19 to the sensor/encoder 80. After modification, servo horn 64 is attached to the output gear 65 which sits on the proximal end 74 of adapter 70. The diameter of the second positioner 73 is slightly bigger than and can not pass through the hole on the top cover 67, therefore preventing the adapter 70 from going through the cover. A hole is made at the bottom cover 61 of the servo 19 such that the distal end 71 can pass through it so that the adapter 70 is parallel to the rotational axis of the output gear 65. The diameter of the first positioner 72 is slightly bigger than the hole such that the positioner 72 cannot pass through the hole in the bottom cover 61 of the servo 19. The part of the distal end 71 that extends out of the bottom cover 61 passes through the middle hole of the rotating disk of encoder 80, such that the rotation of the output gear 65 and horn 64 cause the disk of the encoder 80 to rotate exactly the same amount.

Figure 6:
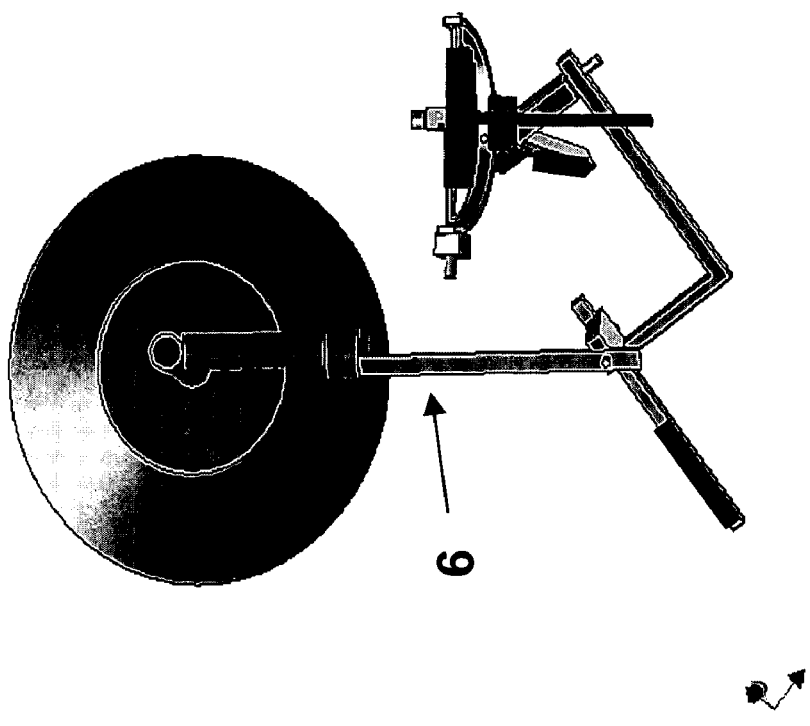
FIGS. 6, 7 and 8 provide examples of real-time cardiac imaging to illustrate how the 6-DOF aspect of the present invention enables the operator to establish the location of imaging planes relative to standard planes used in cardiology referenced to the anatomy.
Figure 6:
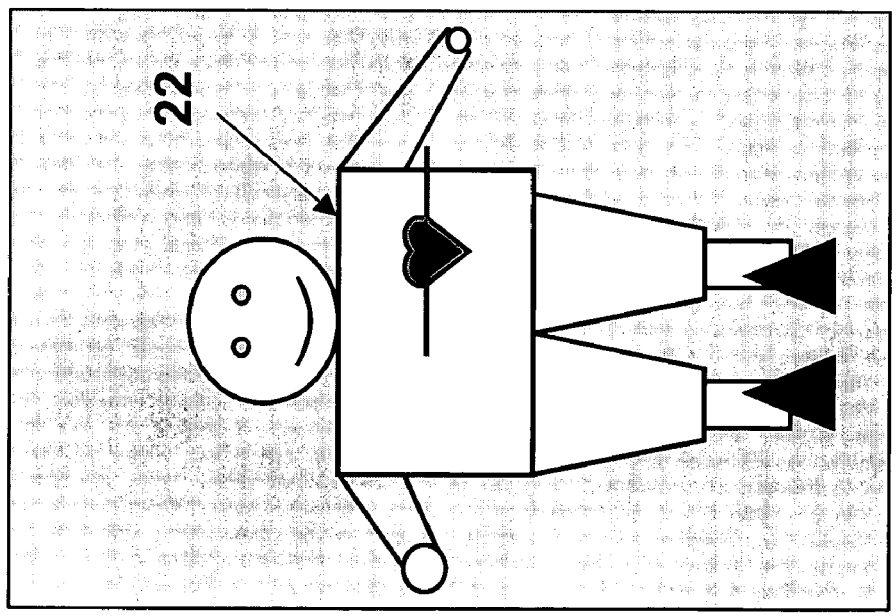
Figure 7:
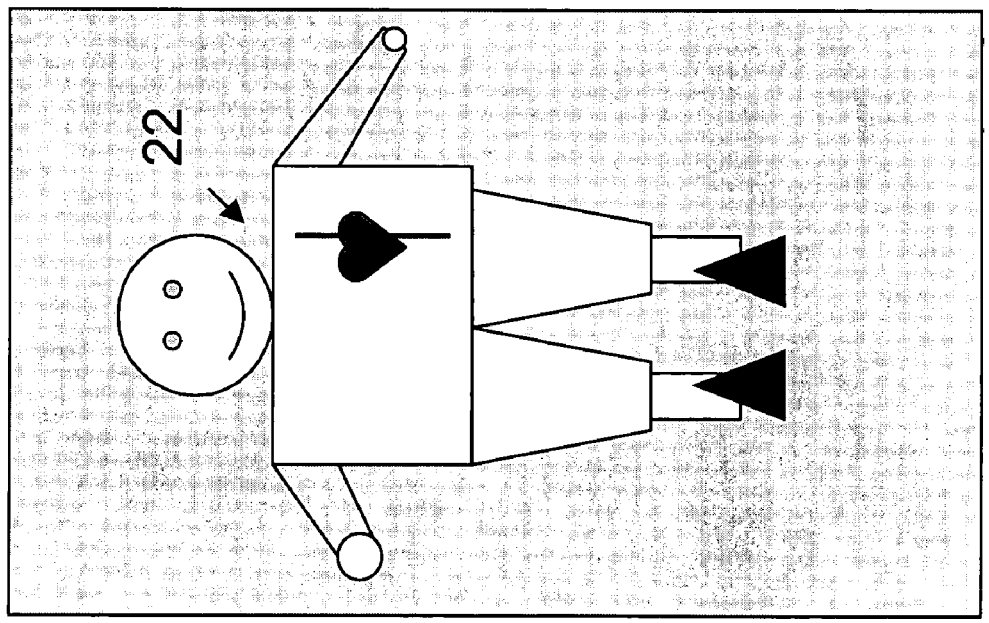
Figure 7:
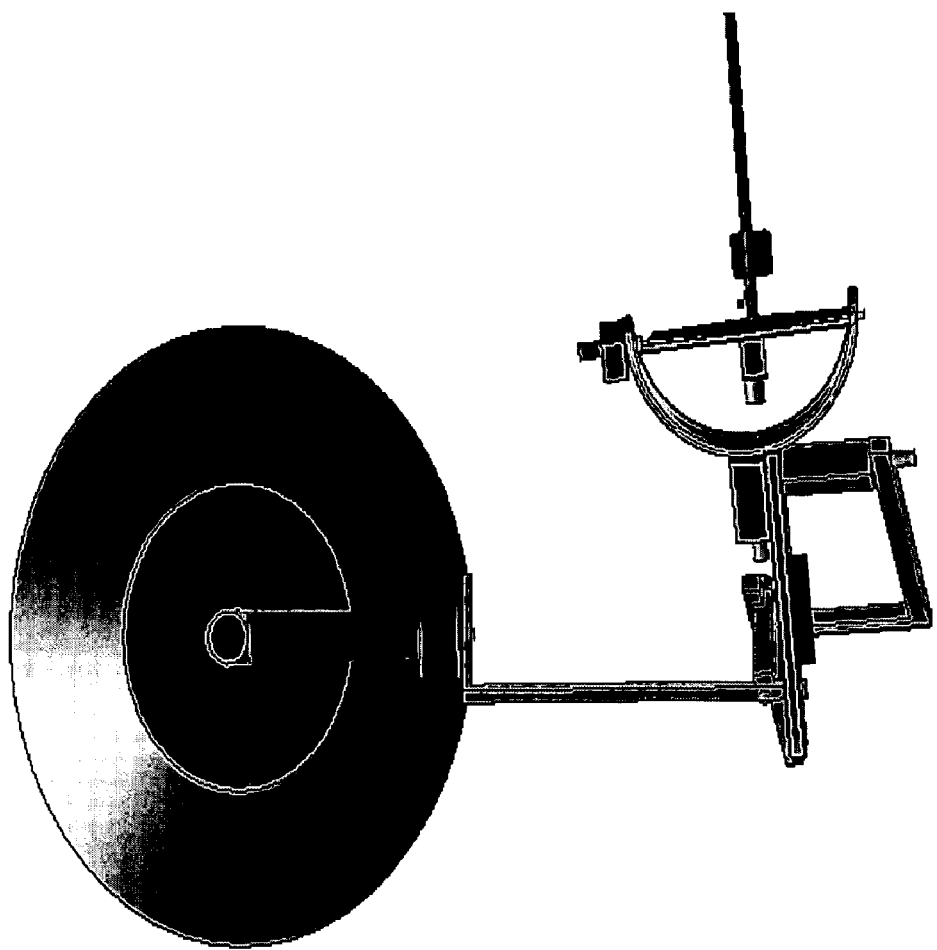
Figure 8:
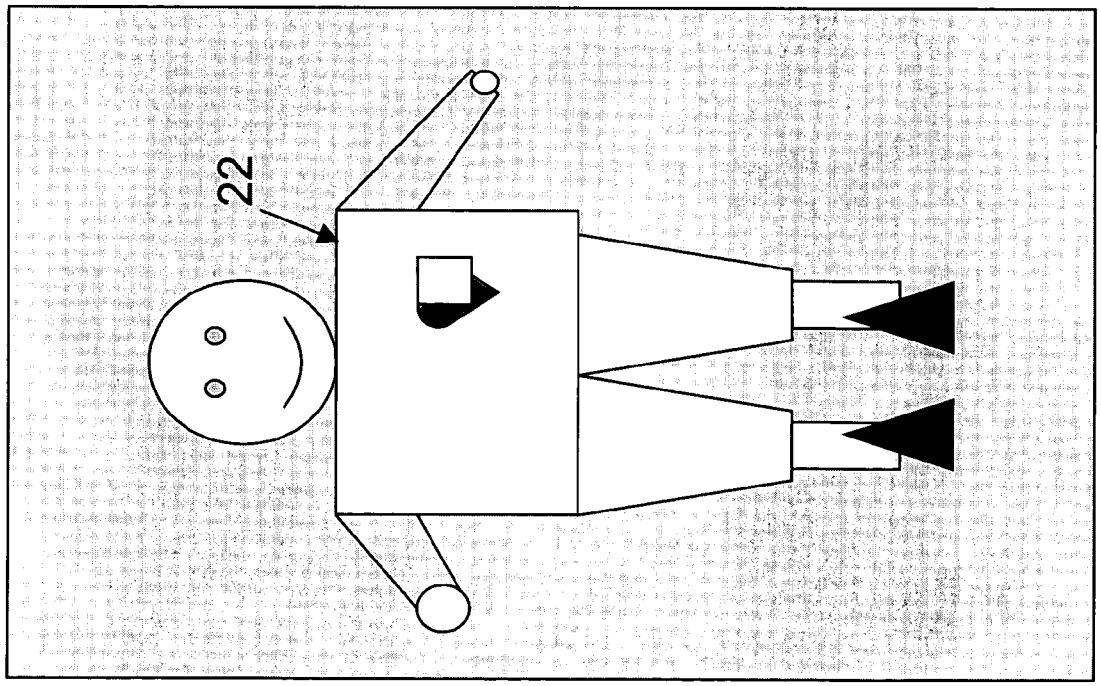
Figure 8:
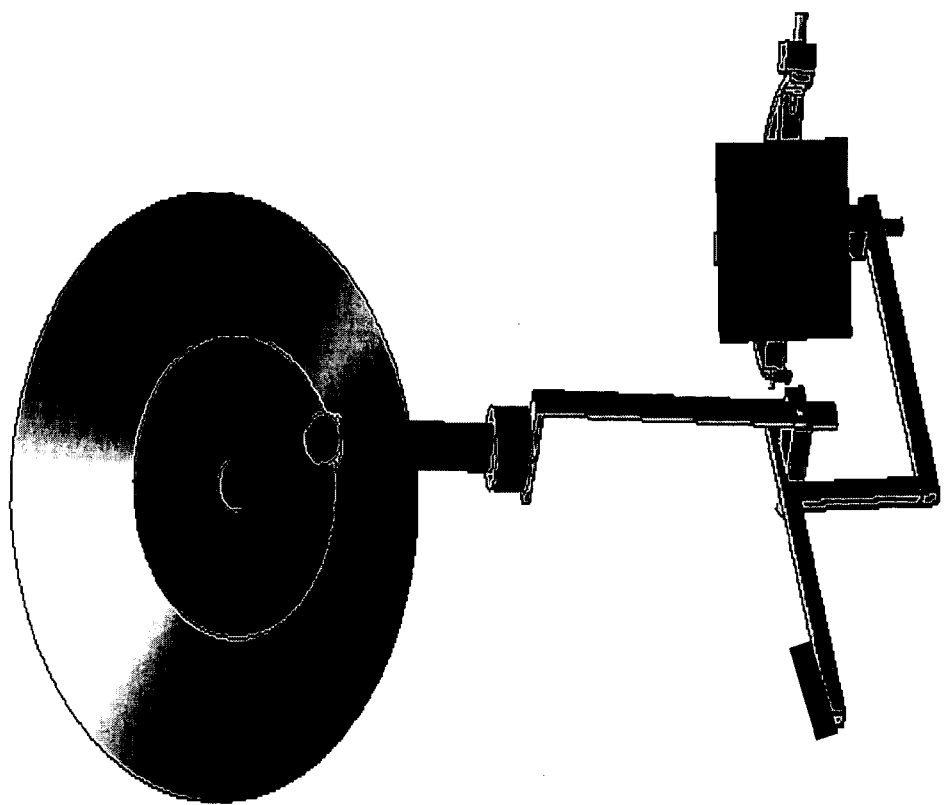

As illustrated in FIGS. 6, 7 and 8, the first linkage 6 is parallel to the surface of desktop. When it is properly configured to a supine patient 22, the mechanical support of the first linkage 6 can represent the back of the patient 22. The geometrical configuration of the device enables the operator to have a reference coordinate fixed on a supine patient, with head close to the base. When imaging the cardiac axial, sagittal and coronal planes, the surface is orientated as shown in FIGS. 6, 7 and 8 respectively. This is intuitive for the operator to establish the location of imaging planes relative to standard ones used in cardiology referenced to the known anatomy of the heart.

Figure 9:
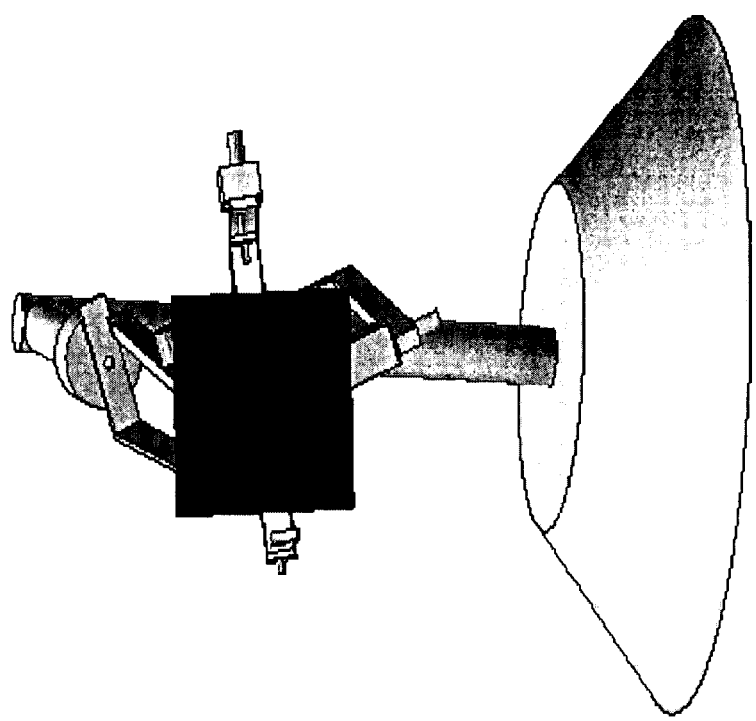
FIG. 9 depicts one example of a computer screen used to program the location and orientation of the surface and during real-time MRI imaging, or other imaging.
Figure 9:
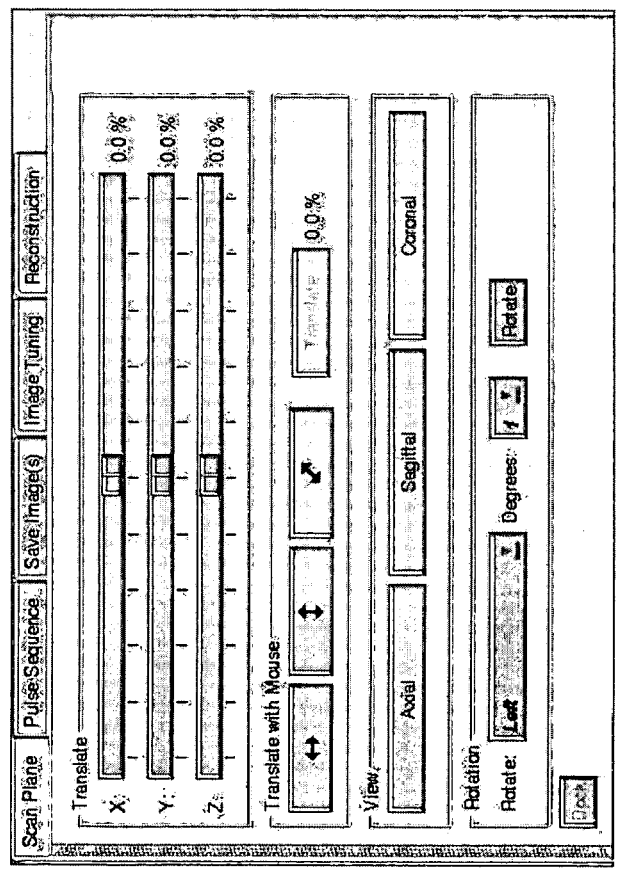

FIG. 9 shows one type of computer screen that can be used to program x, y and z coordinates as well as the pitch, yaw and roll. In FIG. 9, three sliders are used to program the x, y and z coordinates. The operator uses the "Rotate" and "Degree" buttons to program the pitch, yaw and roll. Alternatively, the computer screen may use six sliders or any combination of sliders and buttons to achieve the goal of programming the desired coordinates and orientation. FIG. 9 illustrates one example of how the mechanical armature can automatically follow the prescribed translation and rotation of the MRI scan plane.

A key feature of the invention is that it allows for both input and output control. In a preferred embodiment, a free software package for visualization (VTK, Kitware USA) is used for graphical image rendering. According to the invention, a pre-acquired volume image of the object is volume rendered by texture map and displayed on a standard flat computer screen. The space occupied by the volume is registered through simple scaling to part of the workspace of the 6-DOF device. The scan plane that is to be physically represented (in the case of output) or to be manipulated by the 6-DOF (in the case of input) is also graphically displayed as a cutting plane relative to the volume rendered image. In a preferred embodiment, the image at the cutting plane is also rendered in a separate window to give the operator some feedback on the structure of the object. In a further preferred embodiment, Tk/TCL is used for generating various user interfaces such as sliders and buttons for call back functions. In a particularly preferred embodiment, Real Time Linux is used to write the driver to drive the motors 19. According to the invention, several developed algorithms can be used to rotate the motor shafts to reach the destination based on the angular position of the destination and current position of a motor. This feature of the present invention eliminates the need for a multi-degree motor controller, which can be quite expensive for high degree-of-freedom devices.

The method of the invention can be further characterized by way of additional preferred embodiments. In some situations it is desirable to restrict the movement of the stylus 4 along a pre-specified path. A few non-limiting examples include restricting the motion of the MRI scan plane to a direction perpendicular to the plane, to the left/right, or to up/down, along the short-axis or long-axis of a heart or other organ. In surgical interventions, it is often desirable to restrict the movement of a surgical tool, for example, a catheter, to a certain trajectory, such as a cylinder towards a target tissue. For motion design in computer animation, there are many more similar applications.

In accordance with the method of the present invention, there are at least three possible ways to constrain the input. The first way to constrain input is to encompass haptic force-feedback functionality in the armature by rendering forces at the appropriate point in time. For example, a monotonic function of the 3D vector can be rendered between the ideal point on the specified path and the current actual user manual input. Forces can be applied to the user to guide the user input towards the specified path, wherein the user can freely specify the moving speed along the path.

A second way to constrain the input is to place a physical representative of the desired path within the workspace of the armature. Examples include a straight steel wire to indicate a straight path, or a spring to indicate a cylindrical path.

According to the invention, the user can then manually move the stylus along the physical path, while freely specifying the moving speed along said physical path.

A third way to constrain the input is to use the output functionality to put constraints on input positions. After each manual movement with the stylus 4, the user can withdraw his hand and allow the armature to automatically revert to its output mode. The software will use the user's current input to determine the ideal position on the pre-specified path within identified constraints, and automatically adjust the stylus position towards the pre-specified path. When the user's hand holds the stylus during the next movement, the device automatically switches into its input mode and the user can freely moves the stylus towards the next position, which approximates the pre-specified path before releasing his hand. The device will then automatically adjust itself and dissipate any discrepancy between its current user input position and the ideal path. On this basis, inputs provided by the user are automatically adjusted and follow the pre-specified path. However, in the method of the invention, the user can still adjust the moving speed along any desirable path.

Clinical applications of the present invention can be broadly divided into diagnostic MR imaging and interventional MR imaging. Artifacts due to patient movement are often a major problem in diagnostic MR imaging. With high-resolution scanning, which may require image acquisition over many seconds and even minutes, patient movement and breathing may induce motion artifacts and blurred images. According to the present invention, real-time determination of the location and orientation of the scanned object can reduce the effect of motion on MR scans by real-time control and correction of the scanning plane. The system disclosed by the present invention is particularly useful for various diagnostic and interventional procedures within the cardiovascular system (heart chambers, coronary arteries, blood vessels), the gastro-intestinal tract (stomach, duodenum, biliary tract, gall bladder, intestine, colon) and the liver, the urinary system (bladder, ureters, kidneys), the pulmonary system (the bronchial tree or blood vessels), the skeletal system (joints), the reproductive tract, and other organs and organ systems.

The method of the invention will now be further described by way of a detailed example with particular reference to certain non-limiting embodiments related to interventional MRI applications and to the accompanying drawings in FIG. 1 to 9. It should be understood by those of ordinary skill in the art that the invention can also be employed with only minor variations for anatomic and physiological MRI applications.

Minimally invasive interventional procedures require either direct visual viewing or indirect imaging of the field of operation and determination of the location and orientation of the operational device. For example, laparoscopic interventions are controlled by direct viewing of the operational field with rigid endoscopes, while flexible endoscopes are commonly used for diagnostic and interventional procedures within the gastrointestinal tract. Vascular catheters are manipulated and maneuvered by the operator, with real-time X-ray imaging to present the catheter location and orientation. Ultrasound imaging and new real-time MRI and CT scanners are used to guide diagnostic procedures (e.g., aspiration and biopsy) and therapeutic interventions (e.g., ablation, local drug delivery) with deep targets.

The ideal system for minimally invasive procedures would provide real-time, 3-D imaging as feedback to the operator for optimal insertion and intervention. Such a system should also implement flexible, miniaturized devices, which are remotely sensed to provide their location and orientation. By combining a composite image of the field of operation and the device location and orientation, the operator could navigate and manipulate the device without direct vision of the field of operation and the device.

In one preferred embodiment of the present invention, real-time computer control is provided to maintain and adjust the position of the treatment system and/or the position of the patient relative to the treatment system. In a closely related embodiment, the invention provides real-time computer control of the operation of the treatment system itself. Types of treatment systems suitable for use with the present invention include surgical tools and tissue manipulators, devices for in vivo delivery of drugs, angioplasty devices, biopsy and sampling devices, devices for delivery of RF, thermal, microwave or laser energy or ionizing radiation, and internal illumination and imaging devices, such as catheters, endoscopes, laparoscopes, and the like instruments, or a combination thereof.

The method and apparatus of the present invention can be used with a variety of interventional MRI devices, including tools for minimally invasive surgery, endovascular catheters, rigid and flexible endoscopes, and biopsy and aspiration needles. The invention facilitates localization of the device with respect to the MRI coordinate system and allows the MR scanner to present the device location on the MR images as visual feedback to the operator, or to facilitate calculation and display of the line of current orientation to assist the operator to steer the device into a specific target. The method of the invention can also be used to effectively slave the MRI plane of imaging to the tracking sensor. This embodiment would benefit high resolution imaging on a small volume around the site of a catheter, and would also be useful for imaging of the region-of-interest to improve diagnostic performance or to control the effect of an intervention (e.g. radio-frequency, cryo, or chemical ablation and laser photocoagulation using temperature-sensitive MR imaging).

As another non-limiting example of the benefits of the present invention, the clinical utility of the mechanical armature can be illustrated by reference to its use in guiding the tip of a stem cell delivery catheter towards a tissue target. It is now well established in the medical literature that stem cell therapy has significant clinical potential. Two documented examples of potential benefits of stem cell therapy include (i) treatment of Parkinson's disease symptoms by transplanting dopamine secreting cells into the striatum of the brain and (ii) induction of cardiomyogenesis by delivering mesenchymal stem cells to reversibly ischemic myocardium following myocardial infarction. A specialized catheter that is visible on MRI is used for the delivery of stem cells. During the stem cell delivery process, real time MRI is used to capture the dynamic change of the target position and the position and orientation of the catheter tip as its approaches the target tissue.

The therapeutic efficacy of stem cell interventions is directly influenced by the extent to which viable stem cells are accurately delivered to target tissue locations. Accurate targeting and cell placement generally requires continuous visualization of the tip of the catheter as well as its orientation relative to the target tissue. A number of alternative movements of the catheter tip relative to its location and orientation are possible during cell delivery, including movement of the catheter forward and backward along the tangent direction of its tip segment; movement left or right; movement up or down; and movement along its long axis. Real-time knowledge of any changes in catheter tip position and orientation relative to the target is required in order to adjust the catheter tip to approach the target safely and accurately.

The improved spatial and temporal resolution of real-time MRI now makes it possible to track both the target and the catheter and establish their respective positioning information. However, even with the best visualization methods offered by computer graphics, such as volume rendering, bi-plane, or tri-plane display techniques, the interventional radiologist or cardiologist performing the catheterization procedure generally still finds that it requires excessive mental processing to visualize the distance and orientation of the catheter tip relative to the target. The system of the present invention addresses the visualization problem in a practical manner by integrating the required fine visual-motor control with the motor performance of the operator resulting in substantially improved control and steering of the catheter tip towards the target.

The practical medical benefits of the present invention can be further illustrated by reference to its application to stem cell therapy for reversible myocardial ischemia. In this non-limiting example, the target for stem cell delivery is the border zone ("ischemic penumbra") of the injured myocardium. The target plane is the prescribed MR imaging scan plane that continuously tracks the dynamically changing target. Both the target tissue and the target plane are continuously moving due to cardiac and respiratory motion and the insertion of a catheter. Once the workspace of the armature, the patient space, and the image from the imaging scanner are registered, the mean position of the target and mean orientation of the target plane can be obtained by averaging target position and target plane orientation over time. As one means of providing a physical representation of the target, a paper plane can represent the mean of the target plane, with a circled dot on the paper indicating the mean location of the target. The paper can be manually placed within the workspace of the armature to visually indicate the target position and target plane orientation. The accuracy of the manual placement can then be verified by the output mode of the armature.

With a physical representation of the target tissue established, the stylus 4 can now represent the tip segment of the catheter. Assuming that the world coordinate system, which characterizes the workspace of the armature 1, is moving at the same speed and in the same direction as the target at any point of time, the position and orientation of the stylus relative to the circled dot reflects precisely the relative position and orientation of the catheter tip to the target tissue at any point of time. The relative positioning information provided by the armature 1 can be easily visualized by the interventional radiologist or cardiologist because it is directly visible in a fixed absolute reference coordinate, and there is no need to slide the display planes for better visualization of the catheter tip in case of multi-plane techniques. The position of the stylus 4 is determined from the position of the catheter tip minus the movement of the target from its mean position. The orientation of the stylus 4 is the actual orientation of the catheter tip. The armature can automatically deliver the stylus 4 to its destination position and orientation. Therefore, the stylus 4 constantly reflects the position and orientation of the catheter tip relative to the target. When the physician is ready to advance the catheter tip towards the target, he can simply grasp the stylus 4, align it with the target, and then approach the target.

According to the invention, techniques disclosed in the prior art provide a method means of converting the positioning information provided by the armature 1 into a current signal which can be used to steer the catheter tip. See, for example, T P L Roberts et al., Magnetic Resonance in Medicine, Vol. 48, No. 6, December 2002, p. 1091.

The method of the present invention thus provides integration of input and output functionality of the armature to achieve visualization and navigation of the catheter tip toward the target in an intuitive and efficient way (though the catheter can also be manually manipulated and steered towards the target).

In the method of the present invention, during the visualization and motor action loop, the physical representation of the catheter, i.e. the stylus 4, is fixed on the target. However, this frame and the physical coordinate frame that is fixed on the patient only differ by a translation vector resulting from the target movement. Hence the orientation of the stylus still represents the orientation of the catheter in the fixed physical coordinate. In situations where the target moves very slowly, such as brain tissue, the stylus 4 actually faithfully reflects the catheter tip with respect to its position and orientation in the real physical world relative to the target tissue. At the other extreme, when the target moves significantly, a simple switch to the physical coordinate frame from the relative coordinate frame enables visualization of the localization information in the real patient domain.

It should be understood that the foregoing descriptions are merely illustrative of the invention. Various alternatives and modifications can be devised by those skilled in the art without departing from the scope or spirit of the invention. Accordingly, the present invention is intended to embrace all such alternatives, modifications and variances which fall within the scope of the appended claims.

We claim as our invention:

1. An apparatus and software for manipulating real and virtual objects in three-dimensional space, comprising:
   a mechanical armature, comprising:
     a surface and a stylus movably connected to mechanical linkages and rotational joints so that the stylus and surface may have a location and orientation with six degrees-of-freedom;
     a sensor at each rotational joint to determine the location and orientation, of the mechanical linkages and rotational joints;
     a motor at each rotational joint to rotate the joint and move the mechanical linkage;
   a computer for receiving, sending, and processing the location and orientation information from each sensor;
   an output mode whereby the motors change the location and orientation of each rotational joint, if required, to move the surface and the stylus to a programmed location and orientation so that the armature provides a physical representation of a virtual object;
   an input mode whereby an operator moves the stylus, the sensors provide the location and orientation of each rotational joint to the computer, and the computer displays a two-dimensional representation of the armature.

2. The apparatus of claim 1 wherein weight balancing blocks, the motors' holding torque, and friction maintain the location and orientation of the stylus.

3. The apparatus and process of claim 1, wherein the armature and software provides image-based co-registration algorithms that can be easily validated.

4. The apparatus and process of claim 1, wherein the surface and stylus of the armature may be manipulated in three-dimensional space and the software provides a two-dimensional image of a scan plane, which is useful for image navigation.

5. The process of claim 4, wherein said surface manipulation in three-dimensional space can be used for image navigation based on spatial information from a 4×4 matrix contained in a header file of each image.

6. The apparatus and process of claim 4, wherein said surface and stylus manipulation, and image navigation can be used for automatic manipulation of a medical device to a given location indicated by three spatial coordinates.

7. The apparatus and process of claim 6, wherein said surface manipulation and image navigation can rotate said medical device to a given orientation indicated by a 3×3 rotation matrix.

8. The apparatus and process of claim 6, wherein said medical device is an ultrasound transducer.

9. The apparatus and process of claim 6, wherein said surface manipulation can be used to integrate the positioning and trajectory of medical devices selected from the group consisting of needles and probes with said image guidance.

10. The apparatus and process of claim 9, wherein said surface manipulation and image navigation can be used to control and integrate the operation of two or more mechanical interventional devices each having six degrees-of-freedom.

11. The apparatus and process of claim 10, wherein said control and integration includes having multiple armatures representing multiple catheters.

12. The apparatus and process of claim 6, wherein said medical device is a magnetic resonance imager, and surface manipulation and image navigation provides magnetic resonance images.

13. The apparatus and process of claim 12, wherein said armature and software provides for control of a scan plane in magnetic resonance imaging.

14. The apparatus and process of claim 13, wherein said armature and software also enables switching between guiding a magnetic resonance scan plane and an ultrasound plane in a three-dimensional acquisition mode.

15. The apparatus and process of claim 13, wherein said armature and software further provides for applications that require accurate registration of magnetic resonance imaging data with data obtained using other imaging modalities using a common coordinate system.

16. The apparatus and process of claim 13, wherein said armature and software is not reliant on operator input or influence during a magnetic resonance imaging procedure.

17. The apparatus and process of claim 13, wherein said armature and software also allows the operator to command the magnetic resonance scanner by inputting the spatial location and orientation of the scan plane relative to the object of a patient in the real world.

18. The apparatus and process of claim 13, wherein the location of anatomic structures in a human body can be accurately detected in said scan plane in said magnetic resonance images.

19. The apparatus and process of claim 13, wherein said armature and software provides for six degree-of-freedom surface manipulation and representation which is useful for both conventional clinical magnetic resonance imaging and functional magnetic resonance imaging studies.

20. The apparatus and process of claim 19, wherein said six degree-of-freedom surface manipulation and representation enables magnetic resonance imaging with the same spatial resolution and orientation in different examinations.

21. The apparatus and process of claim 1, wherein said mechanical armature has six degree-of-freedom surface manipulation and representation.

22. The apparatus and process of claim 21, wherein said mechanical armature can detect and track positional changes in a reference structure that is computationally efficient.

23. The apparatus and process of claim 21, wherein said mechanical armature can generate a physical representation of a two-dimensional scan plane of a magnetic resonance image relative to an object in real patient coordinates.

24. The apparatus and process of claim 21, wherein said mechanical armature has a planar surface that can move automatically to reflect the effects of an operator's action on scan plane prescription.

25. The apparatus and process of claim 24, wherein said armature device can move in a coordinated manner through all six degrees-of-freedom required for the optimal scan plane.

26. The apparatus and process of claim 24, wherein said armature device is capable of statically maintaining its location and orientation, thereby improving spatial awareness so the operator can better appreciate the direction of the next movement.

27. The apparatus and process of claim 26, wherein said improved spatial awareness enables improved visualization by the operator of the object under investigation.

28. The apparatus and process of claim 12, wherein said armature device provides for six degree-of-freedom surface manipulation and representation whose function is independent of the magnetic resonance scanner.

29. The apparatus and process of claim 1, wherein said armature device can be used for the automatic manipulation of a medical device to a given position indicated by three spatial coordinates.

30. The apparatus and process of claim 29, wherein said mechanical armature device can also rotate said medical device to a given orientation indicated by a 3×3 rotation matrix.

31. The apparatus and process of claim 29, wherein said medical device is an ultrasound transducer.

32. The apparatus and process of claim 1, wherein said armature and software provide images for interventional magnetic resonance imaging applications.

33. The apparatus and process of claim 32, wherein said interventional magnetic resonance imaging applications are used to guide and monitor minimally invasive diagnostic and therapeutic procedures.

34. The apparatus and process of claim 1, wherein said armature and software provides integration of input and output functionality of the armature to achieve visualization and navigation of a catheter tip towards a target in an intuitive and efficient way.

35. The apparatus and process of claim 34, wherein said catheter tip can also be manually manipulated and steered towards the target.

36. The apparatus and process of claim 29, wherein said armature under real-time computer control provides support for interventional treatment procedures for use with surgical tools and tissue manipulators.

37. The apparatus and process of claim 29, wherein said armature device under said real-time computer control is used to guide interventional devices selected from the group consisting of interventional devices which deliver RF, thermal, microwave or laser energy, and ionizing radiation.

38. The apparatus and process of claim 29, wherein said armature under said integrated real-time computer control is also used to support internal illumination and imaging devices, such as catheters, endoscopes, laparoscopes, and similar instruments.

39. The apparatus and process of claim 33, wherein said interventional treatment procedures are selected from the group consisting of in vivo delivery of drugs, angioplasty devices, biopsy and sampling devices, image-guided interstitial probe placement, high-temperature thermal therapy, cryotherapy, drug therapy for tumors, localization of non-invasive focused ultrasound probes below a tissue surface for thermal therapy, and subcutaneous or transdural placement of biopsy needles or surgical instruments for minimally-invasive surgery.

40. The apparatus and process of claim 13, wherein said scan plane prescription and image navigation process improves detection of the passage of a contrast agent through of human heart microcirculation.

41. The apparatus and process of claim 13, wherein said scan plane prescription and image navigation process also improves MR perfusion imaging of human organs selected from the group consisting of brain, liver, and other solid internal body organs.

42. The apparatus and process of claim 12, wherein said software provides graphical visual information about an object being imaged, a projected display of a 2-dimensional scan plane, and an expected magnetic resonance image corresponding to a scan plane of the object being imaged.

43. The apparatus and process of claim 42, wherein said software also provides a user interface for control of the magnetic resonance scanner and the six degree-of-freedom hardware, as well as the driver and algorithms that relate to the six degree-of-freedom device.

44. The apparatus and process of claim 1, wherein algorithms can be used to rotate a shaft of said motor to enable reaching a destination based on an angular position of the destination and a current position of said motor, thereby eliminating the need for an expensive multi-degree motor controller.

45. The device claim 1, wherein said mechanical armature comprises:
   a base removably mounted on a surface;
   a first linkage connected to the base through a first rotational joint so that the first linkage is parallel to the surface and can rotate on an axis parallel to the surface;
   a second linkage connected to the first linkage through a second rotational joint so that the second linkage can rotate on an axis perpendicular to the first linkage;
   a third linkage connected to the second linkage;
   a fourth linkage connected to the third linkage through a through a third rotational joint so that the fourth linkage can rotate on an axis perpendicular to the third linkage;
   a fifth half-circle linkage connected to the fourth linkage through a fourth rotational joint;
   a sixth linkage connected to the fifth linkage through fifth rotational joint and an end so that sixth linkage can rotate;
   a surface connected to the sixth linkage through a sixth rotational joint so that the surface can rotate;
   a stylus connected perpendicular to the surface; and
   weight balancing blocks connected to a balance arm and the fourth linkage so that the stylus and surface remain static when released.

46. The device of claim 1, wherein said mechanical armature contains six or more mechanical linkages and six or more rotational joints.

47. The device of claim 45 wherein the distance between the second rotational joint and the third rotational joint is equal to the distance between the second rotational joint and the sixth rotational joint.

48. The device of claim 45 wherein the stylus has one or more ears.

49. The device of claim 45 wherein one or more of the rotational joints has a sensor.

50. The device of claim 49 wherein each sensor is connected to a computer.

51. The device of claim 50 wherein the operator manipulates the stylus or surface to a location and orientation, and software is used to evaluate the data from each sensor so that the location and orientation of the stylus or surface may be computed.

52. The device and process of claim 51 wherein the information provided by the sensors is used by the computer to display on a computer screen a two-dimensional representation of the location and orientation of the stylus or the surface.

53. The device of claim 50 wherein each rotational joint is linked to a motor so that the motor can rotate the joint, and each motor is coupled with a sensor.

54. The device of claim 53 wherein,
   each motor and sensor couple is connected to the computer,
   the operator programs the computer to direct each motor to rotate each joint, and
   each sensor provides feedback to the computer regarding the rotation of the corresponding joint.

55. The device and process of claim 54 wherein the computer controls the location and orientation of the stylus or the surface through a series of positions and orientations.

56. The device and process of claim 5 wherein the computer moves the stylus or the surface through a series of positions and orientations.

57. The apparatus and software of claim 4, wherein the scan plane location and orientation are constrained to a pre-specified range.

* * * * *